United States Patent [19]

Wermuth et al.

[11] Patent Number: 4,677,106
[45] Date of Patent: Jun. 30, 1987

[54] DERIVATIVES OF 4-METHYL 6-PHENYL PYRIDAZINE, ACTIVE ON THE CENTRAL NERVOUS SYSTEM

[75] Inventors: Camille G. Wermuth, Strasbourg; Kathleen Biziere, Clapiers; Horace Davi, St. Gely du Fesc, all of France

[73] Assignee: Sanofi, France

[21] Appl. No.: 811,510

[22] Filed: Dec. 20, 1985

Related U.S. Application Data

[62] Division of Ser. No. 405,169, Aug. 4, 1982, Pat. No. 4,576,946.

[30] Foreign Application Priority Data

Aug. 10, 1981 [FR] France ................. 81 15435

[51] Int. Cl.$^4$ .................. C07D 237/20; A61K 31/50
[52] U.S. Cl. ..................... 514/247; 544/224
[58] Field of Search .................. 544/224; 514/247

[56] References Cited

PUBLICATIONS

LeClerc et al, Chem. Abstracts, vol. 85 (1976), entry 177344w.

Primary Examiner—Donald G. Daus
Assistant Examiner—William A. Teoli, Jr.
Attorney, Agent, or Firm—Scully, Scott, Murphy & Presser

[57] ABSTRACT

The present invention relates to derivatives of 4-methyl 6-phenyl pyridazine of formula:

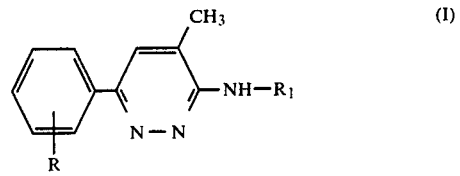

in which
R is OH or H, $R_1$ is H or

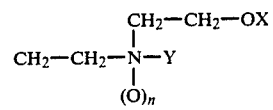

n being 0 or 1, X being H, Y being H or alkyl or X and Y forms an ethylene or oxoethylene group;
it also relates to a process for preparing the products of formula (I) and to drugs containing at least one product of formula (I).

6 Claims, No Drawings

DERIVATIVES OF 4-METHYL 6-PHENYL PYRIDAZINE, ACTIVE ON THE CENTRAL NERVOUS SYSTEM

This is a divisional of copending application Ser. No. 405,169, filed on Aug. 4, 1982 now U.S. Pat. No. 4,576,946.

For numerous years, derivatives of pyridazine have been proposed as drugs. In a large number of cases, these are substances active on the cardiovascular system, presenting in particular an antihypertensive or vasodilator effect. More rarely, an anti-inflammatory and analgesic action has been mentioned among pyridazine derivatives. Finally, French Pat. No. 2 141 697 describes a family of products of general formula:

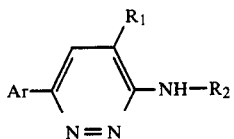

where
  $R_1$ represents hydrogen or a lower alkyl group
  Ar represents an aromatic radical
  $R_2$ designates a

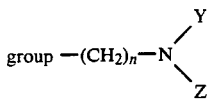

in which n=2 or 3
and Y and Z represent a lower alkyl group or

constitutes a heterocyclic radical.

These compounds are characterized by a psychotherapeutic action of psychotonic type.

A subsequent study of the compound where $R_1=CH_3$, Ar=phenyl and

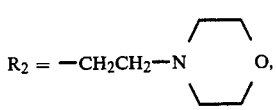

which has received the International Common Denomination "Minaprine", has shown that it is question of a psychotherapeutic action of novel type which has been designated by "disinhibitory" activity. Furthermore, at doses higher than 100 mg/kg per os, this product shows itself to be convulsivant.

It has now been found that certain 6-phenyl 4-methyl 3-amino pyridazines have the same pharmacological and biochemical properties as minaprine, whilst being less toxic and having virtually no convulsivant action.

The invention therefore relates to a family of derivatives of pyridazine of the general formula (I):

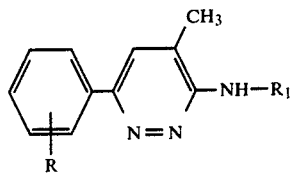

in which:
  R is H or OH
  $R_1$ represents H or the

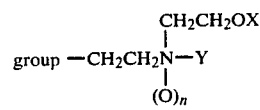

where n=0 or 1
X=H
Y=H or lower alkyl (1 to 4 carbon atoms) or X and Y taken together form an ethylene or oxyoethylene group, with the following conditions:
  X+Y represents an ethylene group only when R represents OH,
  n can be equal to 1 only if X+Y represents an ethylene group.

The present invention also relates to the acid addition salts of the compounds of formula (I), It also relates to a process for preparing the various compounds of formula (I) as well as to the application thereof in therapeutics.

Compounds (I) are generally obtained from a suitably substituted 3-chloro pyridazine.

When $R_1$ is

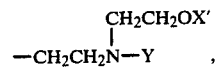

there is reacted on the 3-chloro pyridazine a compound

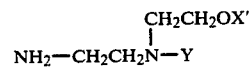

in which Y has the meaning indicated above and X' represents hydrogen or X' and Y together represent an ethylene group.

Reaction between the chlorinated derivative and the amine is generally effected by heating within a suitable solvent such as an alcohol most often at temperature of boiling of the solvent. The duration of the reaction varies from a few hours to several days depending on the nature of the reagents employed. When the reaction proves to be too slow, it may be catalysed by addition of a small quantity of powdered copper.

The reaction is effected in the presence of a hydracid acceptor intended to fix the hydrochloric acid formed in the reaction. An excess of the amine is most often used as such.

Isolation of compound (I) is effected by taking up in water and extraction with a suitable solvent such as ethyl acetate.

When X and Y taken together represent an oxo ethylene group, one has access to the corresponding compounds (I) from the compound (I) in which X and Y are equal to H.

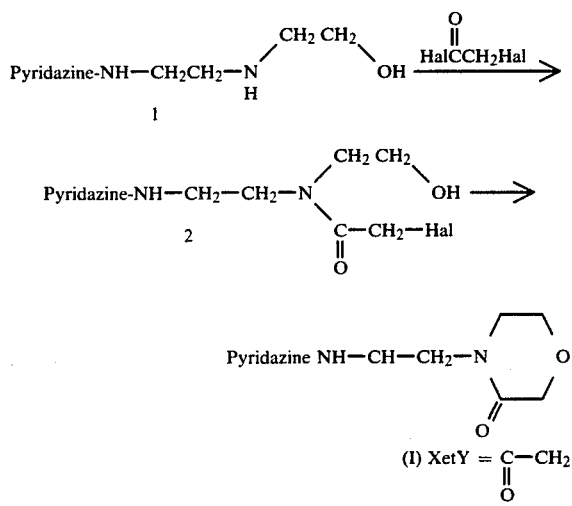

By action of a haloacetyl halide within an inert solvent such as dichloromethane and in the presence of an alkaline agent such as aqueous sodium hydroxide at a temperature of between $-10°$ and $0°$ C., the tertiary amine 2 is obtained. The latter, by action of an alkaline alcoholate such as sodium methylate within methanol at the boiling temperature of the solvent, leads to compound (I) in which X and Y represent an oxo ethylene group. The latter is isolated in the form of a salt such as the hydrochloride.

Similarly, by replacing the haloacetyl halide by ethyl bromoacetate and by operating at reflux of a solvent such as dimethylformamide in the presence of an organic base such as triethylamine, the tertiary amine 3 is obtained.

After saponification of the ester function in acid medium, for example by hydrochloric acid, the expected compound (I) is directly obtained [X and Y representing

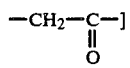

isolated in the form of salt of the acid used.

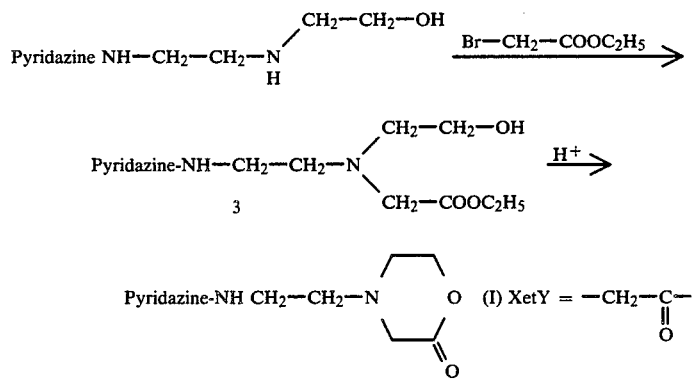

If $n=1$, compounds (I) are obtained from the corresponding compound where $n=0$ by oxidation particularly by action of a per-acid such as para chloro perbenzoic acid within an inert solvent such as chloroform and at a temperature not exceeding 20° C.

When $R_1 = H$, it is not possible directly to obtain the 3-amino pyridazine from the corresponding chlorinated derivative.

In this case, the 3-hydrazino derivative obtained by action at reflux of a large excess of hydrazine on the corresponding chlorinated derivative is employed as intermediary. Hydrogenated in the presence of Raney nickel within a suitable solvent, it leads to the corresponding derivatives (I) $R_1 = H$.

Finally, in all cases when the phenyl in 6 position of the cycle of pyridazine is substituted by an OH group ($R = OH$), it is preferable to prepare, according to the methods indicated previously, the corresponding compound (I) where the phenyl group bears an alkoxy substituent in the same position then to dealkylate this compound by a known method, for example by action of the hydrobromic acid within the acetic acid at reflux.

Compounds (I) thus obtained may be salified in conventional manner by action of the acid on a hot solution of the base, the solvent being chosen so that the salt crystallizes by cooling.

The 3-chloro pyridazines used as starting product are obtained from the corresponding 2H 3-pyridazones by action of an excess of phosphorus oxychloride.

The 2H 3-pyridazones are known or may be obtained by known processes such as the action of hydrazine on γ ketonic acids or derivatives thereof.

The following non-limiting examples are given by way of illustration of the present invention.

EXAMPLE 1

3-[2-(2-HYDROXY ETHYLAMINO)ETHYLAMINO]4-METHYL6-PHENYL PYRIDAZINE, DIHYDROCHLORIDE (CM 30311)

$R = H$; $R_1 = CH_2CH_2NH—CH_2CH_2OH$

A mixture of 7.7 g of 3-chloro 4-methyl 6-phenyl pyridazine and 15 g of N-(2-hydroxy ethyl)ethylenediamine in 50 ml of n-butanol in the presence of 2 g of powdered copper, is taken to reflux for 48 hours. The reaction mixture is poured into 100 ml of water and extracted with ether.

The ethereal phase is extracted with a solution of sulfuric acid SN. The aqueous phase is rendered alkaline by addition of sodium hydroxide in pastille form.

The crystals are drained and recrystallized in the isopropyl ether-isopropanol mixture. m.p.: 91° C.

Dihydrochloride: 3.9 g of the base are dissolved in hot isopropanol then 2.44 ml of concentrated solution of hydrochloric acid are added; by cooling, the hydrochloride crystallizes. It is drained and recrystallized in isopropanol. m.p.: 144° C.

By operating as in Example 1, but by replacing the N-(2-hydroxy ethyl)ethylene diamine by an equivalent quantity of N₁-ethyl N₁(2-hydroxy ethyl)ethylenediamine, the 3-{2-[N-ethyl(2-hydroxy ethylamino)]ethylamino}4-methyl 6-phenyl pyridazine (SR 95084) is obtained in the same way, isolated in the form of dihydrochloride; very hygroscopic product decomposing from 140° C.

EXAMPLE 2

3-[2-(3-OXO 4-MORPHOLINYL)ETHYLAMINO]4-METHYL 6-PHENYL PYRIDAZINE, HYDROCHLORIDE (CM 30488)

R=H;

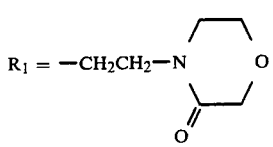

5.4 g of CM 30311 (Example 1) are dissolved in 100 ml of dichloromethane then a solution of 8 g of sodium hydroxide in 100 m of water, is added. The mixture is cooled to −10°, −5° C. and 2.2 g of chloroacetyl chloride are added drop by drop with vigorous stirring.

Stirring is continued for 12 hours then the product is evaporated to dryness. The residue is dissolved in 50 ml of anhydrous methanol and a solution of sodium methylate obtained by action of 0.46 g of sodium on 50 ml of methanol is added. The product is heated to reflux for 6 hours then evaporated to dryness. The residue is taken up in water and extracted with ethyl acetate.

The solution is dried and evaporated to dryness; an oil is obtained.

Hydrochloride: The base is dissolved in the minimum of hot isopropanol and an equivalent of concentrated aqueous solution of hydrochloric acid is added. Ether is added and the product is left to crystallize. m.p.: 190°–191° C.

EXAMPLE 3

3-[2-(2-OXO 4-MORPHOLINYL)ETHYLAMINO]4-METHYL 6-PHENYL PYRIDAZINE, DIHYDROCHLORIDE (CM 30489)

R=H;

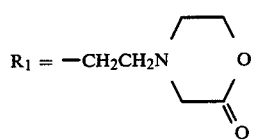

2.7 g of CM 30311 (Example 1) are dissolved in 50 ml of dimethylformamide and 1 g of triethylamine and 1.7 g of ethyl bromoacetate are added. The product is taken to reflux for 1 hour. Water is added, the product is rendered alkaline and extracted with ethyl acetate. The solvent is evaporated to dryness and chromatographed over silica column. By eluting with ethyl acetate, a yellowish oil is obtained.

1 g of this oil is dissolved in 20 ml of aqueous solution of 3N hydrochloric acid and the product is taken to reflux for 14 hours. The solution is washed with ether, then the aqueous phase is evaporated to dryness. The residue crystallizes in ether, m.p.: 170°–2° C.

EXAMPLE 4

3-(2-MORPHOLINO ETHYLAMINO) 4-METHYL 6-(4-HYDROXY PHENYL)PYRIDAZINE DIHYDROBROMIDE (CM 30366)

R=4-OH;

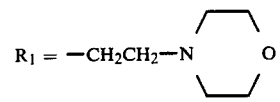

(a) 3-(2-Morpholino ethylamino) 4-methyl 6-(4-methoxy phenyl) pyridazine

Operation is carried out as in Example 1, replacing the N-(2-hydroxy ethyl) ethylenediamine by an equivalent quantity of 2-morpholino ethylamine and the 3-chloro 4-methyl 6-phenyl pyridazine by a corresponding quantity of 3-chloro 4-methyl 6-(4-methoxy phenyl) pyridazine.

In the same way, the product is isolated in the form of dichlorohydrate. m.p. 225° C.

(b) CM 30366

19 g of the base released from the hydrochloride obtained hereinabove, in 150 ml of a 2-1 (vol/vol) mixture of 48% hydrobromic acid and acetic acid are taken to reflux for 6 hours.

The product is evaporated to dryness. A brown oil remains which crystallizes in an ethanol-ether mixture. The crystals are drained and recrystallized in ethanol at 95; m.p. 162° C.

By operating as in Example 4a) from the 3-chloro 4-methyl 6-(2- or 3-methoxy phenyl) pyridazines then by demethylating the products thus obtained according to the method of Example 4b), the following are respectively obtained:

3-(2-morpholino ethylamino) 4-methyl 6-(2-hydroxy phenyl) pyridazine (SR 95070) isolated in the form of dihydrobromide; m.p. 170° C. (decomposition).

3-(2-morpholino ethylamino) 4-methyl 6-(3-hydroxy phenyl) pyridazine (SR 95082) isolated in the form of dihydrobromide; m.p.: 180° C. with decomposition.

EXAMPLE 5

N-OXIDE OF 3-(2-MORPHOLINO ETHYLAMINO 4-METHYL 6-PHENYL PYRIDAZINE (CM 30490)

(I) R=H;

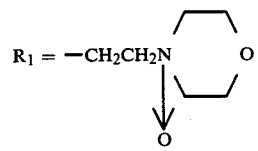

1.5 g of 2-morpholino 3-ethylamino 4-methyl 6-phenyl pyridazine are dissolved in 100 ml of anhydrous chloroform. 0.90 g of para chloro perbenzoic acid is then added and the product is left for 48 hours at ambient temperature. The organic solution is washed with an 10% aqueous solution of sodium bicarbonate. The solution is dried and evaporated to dryness; the residue crystallizes by addition of ether. The product is recrystallized in the mixture of ethyl acetate-hexane.

1 g of crystals is obtained. m.p. with decomposition from 150° C.

EXAMPLE 6

3-AMINO 4-METHYL 6-PHENYL PYRIDAZINE (HYDROCHLORIDE) (CM 30465)

(I) $R=R_1=H$ (a) 3-Hydrazino 4-methyl 6-phenyl pyridazine

The mixture of 5 g of 3-chloro 4-methyl 6-phenyl pyridazine and 12 ml of hydrazine hydrate is taken to reflux. After one hour thirty minutes, the reaction medium is left to cool. A solid separates, which is drained and washed with a little water. The product is recrystallized in the mixture of isopropanol-isopropyl ether. Weight 4.5 g. m.p.: 162° C.

(b) CM 30465

6.5 g of the preceding derivative are dissolved in the minimum of methanol and 2.5 g of Raney nickel are added. Hydrogenation is effected under a pressure of 5 atmospheres for 48 hours. The catalyst is filtered and evaporated to dryness. The residue is recrystallized in a mixture of isopropanol-isopropyl ether. Weight 5.25 g. m.p. 130°-2° C.

Hydrochloride: To 2 g of base dissolved in the minimum of isopropanol are added 1.2 equivalents of gaseous hydrochloric acid then the product is precipated by addition of ether. A white powder is obtained (1.7 g). m.p. 172°-4° C.

By operating as in Example 6a) from 3-chloro 4-methyl 6-(4-methoxy phenyl) pyridazine, the corresponding 3-hydrazino derivative is obtained. The latter treated as in Example 6b) furnishes the corresponding 3-amino derivative.

Finally, by demethylation as in Example 4b), 3-amino 4-methyl 6-(4-hydroxy phenyl) pyridazine (SR 95087) is obtained, isolated in the form of hydrobromide; m.p.: 260° C. (decomposition).

The products according to the invention were subjected to pharmacological tests with a view to determining their activity on the central nervous system and the toxicity thereof.

ACUTE TOXICITY

The products to be studied were administered by the intraperitoneal route in increasing doses to batches of 10 mice. The mortality provoked by the products studied was noted during the 24 hours following administration of the product.

From the results obtained, the lethal dose 50, i.e. the dose provoking the death of 50% of the animals studied, is determined for each of the products studied.

During the same experiments, the convulsivant threshold dose of the product is also noted, i.e. the minimum dose for which a convulsivant activity begins to show.

The results obtained are shown in Table I. This Table shows by way of comparison 2 products described in French Pat. No. 2 141 697 cited above:

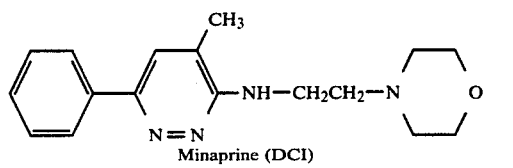
Minaprine (DCI)

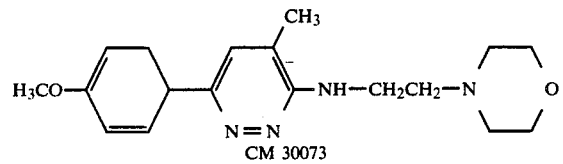
CM 30073

The figures shown in Table I indicate that the products according to the invention present a toxicity and a convulsivant action much less than those of the reference products.

TABLE I

| Compound | $LD_{50}$ (mg/kg; i.p.) | Convulsivant threshold dose (mg/kg; i.p.) |
|---|---|---|
| Minaprine | 63 (52–77) | 35 |
| CM 30073 | 19 (11–35) | 5 |
| CM 30311 | >200 | 200 |
| CM 30366 | >200 | 200 |
| SR 30488 | >300 | 300 |
| SR 30465 | 226 | 200 |
| SR 30490 | >200 | 300 |
| SR 95070 | >200 | 200 |
| SR 95082 | >200 | >200 |
| SR 95084 | 100 < $LD_{50}$ < 200 | 200 |
| SR 95087 | >200 | >200 |

ANTIDEPRESSANT ACTIVITY

Despair reaction

This test was carried out on the female mouse, CDI (Charles River), weighing 18 to 23 g, according to the method described by Porsolt (Archives Internationales de Pharmacodynamie, 1977, 229, 327–336).

The principle of this test is as follows: when a mouse is placed in a narrow recipient filled with water, it struggles, then, after 2 to 4 mins., it becomes still and floats on its stomach, its back rounded, its rear paws drawn up under its body and it makes only a few movements necessary for holding its head out of the water. This is the so-called despair reaction.

Certain psychotherapeutic agents, particularly antidepressants, extend the time during which the mouse struggles.

The following protocol was chosen: The products to be studied were administered by the i.p. route 1 hour before the test. For the test, the animals are placed in a narrow recipient (10×10×10 cm) filled with water up to a height of 6 cm, the temperature of the water being 24° C.±2° C. The animals are left 6 minutes in the water and the time when the animal remains immobile between the 2nd and the 6th minute is measured—the shorter this time, the more the substance is active.

Each substance was studied on a batch of 10 mice. The results are the average of at least two experiments.

Antagonism of the ptosis induced by reserpine

This test, described by GOURET (Journal de Pharmacologie (Paris), 1973, 4(1), 105–128), was carried out on the female mouse CDI (Charles River) weighing 20±1 g. The reserpine provokes a ptosis one hour after intravenous administration thereof; certain antidepressants oppose this ptosis.

The following protocol was chosen: The substances to be studied were administered by the i.p. route. The reserpine is administered simultaneously by the intravenous route at the dose of 2 mg/kg. One hour after administration of the reserpine, the number of animals not presenting ptosis is noted.

This test was carried out on batches of 10 mice, the results are expressed in percentage of animals not presenting ptosis and are the average of at least two experiments.

The results obtained with the products of the invention are shown in Table II. By way of comparison, the results obtained with the two products of the prior art, Minaprine and CM 30073, have also been indicated.

TABLE II

| | Antidepressant activity | |
|---|---|---|
| Compounds | Antagonism of the ptosis induced by reserpine (ED$_{50}$, mg/kg; i.p.) | "Behavioral Despair" % of reduction of the duration of immobilisation |
| Minaprine | 5 (4–7) | 10 mg/kg: −35%** |
| CM 30073 | 1 mg/kg: 30% 5 mg/kg: 60% product too toxic at higher doses | — |
| CM 30366 | 12 (11–15) | 10 mg/kg: −31%** |
| CM 30465 | 8.6 (8.3–9) | 10 mg/kg: −24%** |
| SR 30488 | 20 (13–31) | — |
| SR 30490 | ≅50 | — |

DOPAMINOMIMETIC ACTIVITY

The depaminomimetic activity of the products of the invention was studied on the striatal dopaminergic receptors of the mouse according to the technique described by P. PROTAIS and J. COSTENTIN, Journal de Pharmacologie (Paris), 7, 251–255 (1976).

The unilateral lesion of the nigrostriatal dopaminergic neurones induces a hypersensitivity of the receptors of the dopamine at the level of the striatum. The resulting asymmetry is revealed by rotations of the animal in the direction contralateral to the most intensely stimulated receptors.

After administration of the products to be studied by the intraperitoneal route, the number of rotations made by the animal is counted for a period of 2 minutes.

The results are expressed in the form of percentage of the variations with respect to the controls not having received the product to be studied.

The results obtained with various products of the invention are shown in Table III which also shows the results of the 2 comparison products: Minaprine and CM 30073.

Tables I, II and III show that the compounds representative of the present invention have, overall, an antidepressant and dopaminomimetic activity of the same order of size as that of minaprine.

With respect to minaprine and especially to CM 30073, the products representative of the present invention are only slightly toxic and have virtually no convulsivant activity.

The new compounds of the present invention may thus be used in therapeutics for all disorders of the psychomotor behaviour.

TABLE III

| COMPOUNDS | Doses μmoles/ kg; i.p. | Average number of ipsilateral rotations in 2 minutes % with respect to controls |
|---|---|---|
| Minaprine | 5.3 | −91% |
| CM 30073 | 5.3 | 0% |
| CM 30311 | 5.3 | −146% |
| CM 30366 | 5.3 | −111% |
| CM 30465 | 5.3 | −89% |
| CM 30488 | 5.3 | −90% |
| CM 30489 | 5.3 | −97% |
| SR 95070 | 5.3 | −89% |

They may be prescribed inter alia for hyperkinesis in the child, for the masked depression in the adult, for serious depressive states, for depression in the elderly and for disorders in the memory and in senescence.

These products may be administered by the oral route or by injectable route. The pharmaceutical compositions may be solid or liquid and be, for example, in the form of tablets, capsules, granulates, suppositories or injectable preparations.

Dosage may vary to large proportions, particularly according to the type and seriousness of the disorder to be treated and depending on the mode of administration. In the adult, by the oral route, it is most often between 0.010 g and 0.500 g possibly distributed in several doses.

By way of example, the following Galenic preparation may be indicated:

| Tablets | |
|---|---|
| CM 30465 | 200 mg |
| Microcrystalline cellulose | 100 mg |
| Lactose | 197 mg |
| Magnesium stearate | 3 mg |
| | 500 mg |

What is claimed is:

1. Compounds of 4-methyl 6-phenyl pyridazine of the formula:

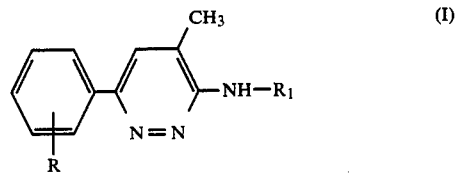

in which:
R is H or OH and
R$_1$ represents H
and the pharmaceutically acceptable acid addition salts thereof.

2. The compounds of claim 1, which are the addition salts of the compounds of formula (I) with a pharmaceutically acceptable acid.

3. A pharmaceutical composition for the treatment of depressive states which contains at least one product of claim 1.

4. A pharmaceutical composition which contains from 0.01 g to 0.500 g of at least one product according to claim 1.

5. A pharmaceutical composition for the treatment of depressive states which contains at least one product of claim 2.

6. A pharmaceutical composition for the treatment of depressive states which contains from 0.01 g to 0.500 g of at least one product of claim 2.

* * * * *